(12) United States Patent
Nuta et al.

(10) Patent No.: US 10,413,720 B2
(45) Date of Patent: *Sep. 17, 2019

(54) APPARATUS FOR ARTIFICIAL CARDIAC STIMULATION AND METHOD OF USING SAME

(71) Applicant: Gloucestershire Hospitals NHS Foundation Trust, Gloucestershire (GB)

(72) Inventors: Bogdan Nuta, Gloucestershire (GB); Ian Lines, Gloucestershire (GB)

(73) Assignee: Gloucestershire Hospitals NHS Foundation Trust (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/391,425

(22) PCT Filed: Apr. 10, 2013

(86) PCT No.: PCT/GB2013/000162
§ 371 (c)(1),
(2) Date: Oct. 9, 2014

(87) PCT Pub. No.: WO2013/153350
PCT Pub. Date: Oct. 17, 2013

(65) Prior Publication Data
US 2015/0088219 A1 Mar. 26, 2015

(30) Foreign Application Priority Data
Apr. 10, 2012 (GB) .................................. 1206289.9

(51) Int. Cl.
*A61N 1/00* (2006.01)
*A61N 1/05* (2006.01)
(Continued)

(52) U.S. Cl.
CPC ................ *A61N 1/056* (2013.01); *A61F 2/82* (2013.01); *A61N 1/368* (2013.01); *A61N 1/3684* (2013.01);
(Continued)

(58) Field of Classification Search
CPC ...... A61N 1/056; A61N 1/368; A61N 1/3756; A61N 1/057; A61N 1/37288;
(Continued)

(56) References Cited

U.S. PATENT DOCUMENTS

| | | | |
|---|---|---|---|
| 6,161,029 | A | 12/2000 | Spreigl et al. |
| 2006/0259088 | A1 | 11/2006 | Pastore |

(Continued)

OTHER PUBLICATIONS

International Search Report for PCT Application No. PCT/GB2013/000162, dated Dec. 5, 2013, 5 pages.

*Primary Examiner* — Mallika D Fairchild
(74) *Attorney, Agent, or Firm* — Christopher McKeon; Jason Saunders; Arnold & Saunders, LLP

(57) ABSTRACT

A system for artificial stimulation of the heart of a subject is provided, the system comprising a controller comprising a receiver for receiving signal data, a processor for processing received signal data, and a transmitter for transmitting signal data; a sensing stent for location in the proximal coronary sinus of the subject, the sensing stent electrode comprising a sensing electrode assembly for sensing atrial and/or ventricular signals from the heart of the subject and a transmitting assembly for transmitting signal data to the receiver of the controller; and a stimulation stent for location in a vein of the subject distal of the sensing stent, the stimulation stent comprising a receiver for receiving signal data from the transmitter of the controller and an electrode assembly for providing a stimulating electrical signal to the heart of the subject in response to the data received.

7 Claims, 10 Drawing Sheets

(51) Int. Cl.
    *A61N 1/372*     (2006.01)
    *A61N 1/375*     (2006.01)
    *A61N 1/368*     (2006.01)
    *A61F 2/82*     (2013.01)

(52) U.S. Cl.
    CPC ....... *A61N 1/3756* (2013.01); *A61N 1/37288* (2013.01); *A61F 2250/001* (2013.01); *A61N 2001/0585* (2013.01)

(58) Field of Classification Search
    CPC . A61N 1/3684; A61N 2001/0585; A61F 2/07; A61F 2/82; A61F 2250/001
    See application file for complete search history.

(56) References Cited

U.S. PATENT DOCUMENTS

2007/0150009 A1    6/2007    Kveen et al.
2008/0288039 A1\*  11/2008    Reddy .................. A61N 1/057
                                        607/122

\* cited by examiner

APPARATUS FOR ARTIFICIAL CARDIAC STIMULATION AND METHOD OF USING SAME

The present invention relates to an apparatus for providing artificial stimulation of the heart of a subject, finding use for example in cardiac pacing and cardiac resynchronisation therapy. The present invention also provides a method for artificial stimulation of the heart of a subject, for example as part of a cardiac pacing or cardiac resynchronisation therapies.

Heart failure is associated with major morbidity and mortality, with the care and treatment of patients with heart failure representing an increasing burden on healthcare resources. Drug therapy for heart failure has become established. However, there are limitations to such therapy, in particular generated by a patient's inability to tolerate different classes of medication and also by compliance issues. Also, most patients tend to experience a plateau in clinical improvement after a variable period of time on optimal medication. Consequently, the rate of re-admissions and hospitalizations for patients suffering from heart failure has increased significantly, with a corresponding increase in the need for healthcare resources.

Cardiac Resynchronization Therapy (CRT) is a well established treatment, in particular for the treatment of patients with advanced heart failure. CRT refers to the principle of synchronizing the left ventricular (LV) and right ventricular (RV) contractions to follow the atrial electrical activity and, in doing so, to eliminate or improve the electromechanical delay associated with electrical conduction deficit, most notably left bundle branch block (LBBB), commonly present in patients with symptomatic advanced heart failure. In practice, current technology only offers CRT using unisite left ventricular pacing. The left ventricle, however, suffers from both intraventricular dyssynchrony (lack of synchrony between the different walls of the ventricle) and interventricular dyssynchrony (lack of synchrony with the right ventricle, in particular due to left bundle branch block (LBBB)).

Currently, the procedure for conducting CRT employs the implantation of one or two connections or leads in the right side of the heart, usually in the right atrium (RA) and right ventricle (RV) chambers, as routinely used for anti-bradycardia pacemakers. In addition an LV lead which is placed through the coronary sinus (CS) into a lateral or posterolateral tributary vein of the coronary sinus on the LV. This LV lead has the ability to sense and pace the left ventricle, the latter being timed with the right ventricle pacing, in order to resynchronize biventricular pacing. A CS sheath is used to deliver the LV lead, typically over a 0.35 mm (0.014 inch) guidewire. After checking the sensing and pacing parameters of the LV lead, the CS sheath is carefully removed allowing the LV lead to remain in position. To minimise the risk of LV lead displacement, various manufacturers have produced differently shaped distal LV lead ends that tend to maximise long term stability in the implanted position.

CRT is now an established interventional treatment for heart failure and is has proven benefits if offered in addition to the established treatment options employing various classes of pharmaceutical agents. However, there are certain limitations with the currently available technology. These limitations relate firstly and principally to the number of leads which can be safely implanted through the veins leading to the heart, but also in the heart itself and its veins. The more leads are used, the higher the risk of vascular complications. Further, the potential for displacement of a lead increases with the number of leads being implanted.

Second, while lead-related infection is relatively rare, increasing the number of devices and leads implanted in a patient in turn increases the risk of vascular and infective complications. If infection occurs, the whole system would have to be removed, including the intracardiac leads. The removal of leads, for example in a system that has been implanted for more than 6 months, can be made very difficult by the adhesions that typically form over time between the leads and the inner wall of the veins in which they are sited. Therefore, the process of extracting leads is potentially dangerous for the patient and can be a complicated procedure. As a result, the removal of leads is only available in a relatively few healthcare centres.

Third, the long term benefits of CRT may be reduced by the fact that only single site (unisite) LV pacing is generally available with the current technology.

As a result, the resynchronisation of the left ventricle is generally limited to the single site where the LV leads can be placed. As noted above, the left ventricle, however, can suffer from both intraventricular dyssynchrony (lack of synchrony between the different walls) and interventricular dyssynchrony (lack of synchrony with the right ventricle due to LBBB). One attempt to address this problem has been the introduction of leads with two or more pacing poles at their distal end. However, such leads do not offer true multisite pacing, as the pacing poles are placed on the distal end of the same lead, in the same vein and cannot be disposed in different veins using a single lead. It would be advantageous of a system could be provided that is capable of treating both types of left ventricular dyssynchrony described above.

Further, the implantation of a CRT device using the most commonly employed over the wire LV lead placement can be limited by variations in the anatomy of the coronary sinus and its tributary veins. In some cases, anatomical variations can result in a paucity of target veins, the presence of valves or very tortuous veins. Although relatively rare, the leads placed on the left ventricle can become displaced after the implant procedure has been completed, with loss of pacing and consequent loss of CRT. Therefore, in order to re-establish an effective CRT for the patient, the LV lead has to be repositioned or otherwise fixed in place. The vast majority of currently available LV leads are passive fixation leads. Re-opening the wound to reposition or replace the displaced LV lead, especially only shortly after the initial procedure has been completed, is undesirable, as it significantly increases the risks of infection.

Still further, once in place, the LV lead can, in some patients stimulate the diaphragm at the same time as stimulating the LV leading to undesirable diaphragmatic twitching. This process occurs when the lead placed on the left ventricle inadvertently stimulates the adjacent phrenic nerve which controls the diaphragm. Occasionally, if the LV lead moves from the original position after the implant, the process of phrenic nerve stimulation with consequent diaphragmatic twitch can occur latently. It may be possible to overcome this complication by appropriate pacemaker re-programming, essentially using different pacing vectors. However, this option is not always available.

Finally, when two or more leads are present in a vein, there is a small risk of a venous thrombosis occurring, and consequent vascular occlusion. If a thrombosis occurs, and is associated with symptoms of impaired blood flow through the affected vein, anticoagulation treatment may have to be considered, often with its associated risks.

Severe impairment and dilation of the left ventricle is a common symptom of patients with advanced heart failure. As a result, multisite pacing of the left ventricle is likely to be more beneficial, in particular by allowing a more efficient reverse remodelling process of the damaged and enlarged left ventricle, to counter remodelling occurring in the heart when it starts to fail. However, the current technology for artificial heart stimulation does not reliably allow this process to be applied, as it requires more than one lead to be placed in the left ventricle, with the attendant problems discussed above.

Examples of lead-based systems for the artificial stimulation of a patient's heart are disclosed in US 2008/0071315, US 2006/0259088, and US 2009/0318989.

It would be advantageous if a system could be provided for artificially stimulating the heart of a patient without the need for leads to be implanted within the vessels in and around the heart of the patient. It would be particularly advantageous if the system could be capable of pacing and re-synchronising the heart of the patient, especially if the system allowed for multi-site pacing of the left ventricle.

The concept of leadless multisite cardiac pacing has been explored. For example, multisite pacing using active fixation mechanisms to attach the leadless pacing devices to a desired fixed location within the heart or on the exterior wall of the heart, as opposed to epicardial venous electrodes has been described. Reference in this respect is made, for example, to U.S. Pat. Nos. 7,650,186 and 7,647,109, which both describe a leadless cardiac stimulation system. The system comprises one or more leadless electrodes that may be implanted at sites close to the myocardium using a percutaneous, transluminal, catheter delivery system.

An alternative approach is disclosed in U.S. Pat. No. 5,814,089, which concerns a leadless multisite implantable stimulus and diagnostic system. A leadless electrode apparatus and system is also disclosed in US 2007/0150009, US 2002/0095191, US 2005/0096702, US 2006/0085039, and US 2007/0088394. An MRI compatible leadless cardiac pacemaker is described in US 2011/0077708. A subcutaneous implantable cardioverter-defibrillator for use with other implantable and external devices for the coordinated delivery of drugs and therapy is disclosed in US 2006/0241701.

The options of placement of right intraventricular leadless electrodes may be feasible, as the function and size of the right ventricle is usually unaffected by heart failure. However, the placement of pacing electrodes in the diseased and, typically, dilated and thinned left ventricular chamber of the heart in patients suffering from heart failure, for example following a large myocardial infarction, is clinically unattractive. This technique may encourage sepsis and thrombosis, which carry potentially very serious consequences for the patient. Further, actively fixing the electrode within the left ventricular wall using a similar technique to that described above may be associated with further damage and possible rupture of the thinned left ventricular wall, making CRT delivery in this way impractical. The alternative placement of electrodes on the outside, as opposed to the inside, of the left ventricle may carry similar risks, in cases where the wall of the left ventricle is severely thinned. This approach is also considerably more invasive to the patient than the percutaneous strategy.

WO 2007/078770 concerns an electrode apparatus, system and method of use. In operation, remote communication is established between a pulse generator and various designs of stented electrodes implanted within target coronary sinus veins on the left ventricle. However, the majority of applications of the system appear to have been intended for either asynchronous non-sensed pacing delivery or to include sensing using conventional right atrial and ventricular leads. Therefore, the system of WO 2007/078770 cannot be considered to be a truly leadless system. In some embodiments, the system of WO 2007/078770 employs some form of sensing delivered via a controller. In an alternative embodiment, the stented electrodes appear to include a sensing mechanism in addition to the pacing mechanism, in order for the sensed activity to be transferred to a controller in communication with the pacemaker itself. However, these stented electrode devices would have to be self powered in order to transmit the sensed signals, significantly increasing their size, in turn making them potentially too bulky to be negotiated into the relatively small target veins of the coronary sinus.

Further, U.S. Pat. No. 6,445,953 discloses the general concept of a wireless pacing system able to stimulate an animal heart. However, there is no mention of any abilities of the system to sense the heart function. Consequently, the lack of synchronous pacing in the absence of appropriate sensing would have adverse haemodynamic effects on the function of the heart. In contrast, all currently available lead-based pacing and CRT systems use atrial sensing as a method to time ventricular pacing for symptomatic bradycardia or biventricular pacing for patients with heart failure.

US 2003/0158584 describes a chronically implanted device for sensing and for providing therapy. A range of embodiments of devices for implanting in the human body are described. In one embodiment, the device comprises a stent implanted in the coronary artery of the heart.

US 208/0021336 discloses a device and method for the accelerometer-based characterisation of cardiac synchrony and dyssynchrony.

U.S. Pat. No. 8,019,419 discloses a method and apparatus for the leadless, battery-free, wireless stimulation of tissue.

EP 1 222 943 concerns a wireless cardiac pacing system comprising vascular electrode stents.

US 2007/0208390 discloses an implantable wireless sound sensor.

It has now been found that an improved system for the artificial stimulation of the heart of a patient comprises a self-powered stent electrode positioned at the origin of the coronary sinus (CS) vein, which will provide both atrial and ventricular sensing from that position. The coronary sinus is a major cardiac vein draining the venous blood of the heart back into the bottom of the right atrium. The coronary sinus has its main body situated between the left atrium and the left ventricle. As a result, a stent electrode placed in the proximal segment of the coronary sinus will sense both atrial and ventricular signals. Pacing delivered to the heart via a stent electrode in the mid to distal segments of the coronary sinus results in atrial, rather than ventricular electrical capture, whilst stented electrodes placed in suitable ventricular target veins emerging from the coronary sinus will provide ventricular or biventricular capture. An advantage of this system is that it is capable of treating both types of left ventricular dyssynchrony described above.

According to the present invention, there is provided a system for artificial stimulation of the heart of a subject, the system comprising:

a controller comprising a receiver for receiving signal data, a processor for processing received signal data, and a transmitter for transmitting signal data;

a sensing stent for location in the proximal coronary sinus of the subject, the sensing stent electrode comprising a sensing electrode assembly for sensing atrial and/or ventricular signals from the heart of the subject and a transmitting assembly for transmitting signal data to the receiver of the controller; and a stimulation stent for location in a vein of the subject distal of the sensing stent, the stimulation stent comprising a receiver for receiving signal data from the transmitter of the controller and an electrode assembly for providing a stimulating electrical signal to the heart of the subject in response to the data received.

The system of the present invention is particular suitable for pacing the heart of the subject and/or for synchronising the heart, in particular for applying cardiac resynchronisation therapy (CRT). The system relies upon a sensing stented electrode for location in the proximal portion of the coronary sinus and operable for sensing purposes only. In this way, the size of the sensing stent may be kept to a minimum, as it is not required to deliver pacing impulses to the heart, but rather merely senses intracardiac signals. The system relies upon one or more stented electrodes located in veins around the heart distal of the sensing stent. For example, as described in more detail hereinafter, the system may comprise a stented electrode located in a mid to distal location within the coronary sinus to pace the left atrium. Alternatively, or in addition, the system may comprise one or more stented electrodes disposed in the coronary sinus, one or more tributary veins thereof and/or the small cardiac vein for stimulation of one or both ventricles. The number and position of such stented electrodes will depend, in part, upon the nature of the stimulation required for the subject and the number and condition of target veins available for locating a stented electrode.

The system comprises a controller. The controller comprises a receiver and is operable to receive signals and signal data from the sensing stent located in the coronary sinus, in particular signal data relating to the electrical function of both the atria and the ventricles of the heart. The controller comprises a processor for processing and interpreting signal data received from the sensing stented electrode in the coronary sinus. The processor further translates these signal data into signals for the one or more stented electrodes disposed in veins distal of the sensing stented electrode to provide electrical stimulation to the heart. In particular, the signals received from the sensing stent in the coronary sinus are typically filtered, amplified and/or processed through a series of digital timers and the resultant signal is used to trigger a pulsed discharge which, in turn, is used to stimulate myocardial cells by way of the one or more stimulation stents. Such processors, their function and operation are known in the art.

Further, the controller comprises a transmitter to provide signals to the one or more stented electrodes, for providing stimulation to the target regions of the heart. The transmitter preferably comprises an antenna for remote communication with the various stents in place in the heart of the subject, without the need for leads.

Suitable controllers are known in the art and include known subcutaneous and subpectoral implantable pulse generators and pacemakers, currently in use for heart pacing.

As noted above, in use the controller communicates with both the sensing stent in the coronary sinus and with the one or more stimulation stents to provide stimulation to the appropriate region of the heart. The controller may communicate with and receive signals from the sensing stent by any suitable means, including a lead. However, it is preferred that the sensing stent is leadless and communicates remotely with the controller in a manner known in the art. Similarly, the controller may communicate with and transmit signals to the one or more stimulation stents by any suitable means, including a lead. However, it is particularly preferred that one or, more preferably, all of the stimulation stents are leadless and communicate remotely with the controller in a manner known in the art.

The controller may be powered by any suitable means. In particular, the controller may comprise one or more batteries for providing electrical power. The batteries may be rechargeable, for example remotely using electrical induction. In such cases, the controller will comprise an induction coil for generating an electrical current under the action of an applied magnetic field, typically provided from outside the body of the subject. Such recharging of the batteries by induction is known in the art, for example in WO 2007/078770. Alternatively, single charge batteries may be employed as is known in the art. Such batteries generally have an extended lifetime, for example of 5 to 10 years, after which the controller is removed from the subject and the batteries replaced, typically with the entire controller unit. Such known techniques are suitable for use in the system of the present invention.

In use, the system may further comprise a programmer, typically external of the subject. The programmer is operable to allow the operation of the controller to be monitored and modified, as appropriate. For example, the programmer may be used to interrogate the controller to determine the operating parameters of the pacing function, such as sensing and pacing impedances and thresholds, and to adjust the operating parameters of the controller as required. Similarly, the programmer may be used to log data relating to the function of the subject's heart received from the controller, for example to conduct arrhythmia logging.

The programmer may communicate with and receive signals from the controller by any suitable communication means, including a lead. However, it is preferred that the programmer communicates remotely with the controller, that is without a lead, in a known manner. Such remote communication is particularly preferred when the controller is located subcutaneously or subpectorally within the subject. Remote radio frequency communication is a particular suitable technique and is known in the art.

Suitable remote communication systems and modalities between the controller and the one or more stimulation stents and/or the programmer are known in the art, for example in U.S. Pat. Nos. 6,366,816; 5,405,367, and 4,886,064. As a further example, U.S. Pat. No. 5,411,535 discloses a cardiac pacemaker in which a supersonic or electromagnetic signal is converted by a piezoelectric transducer into a voltage that a receiver and an amplifier transmit to a remote receiver electrode designed to pace the heart tissue. Remote communication systems, such as those using radiofrequency, infrared, acoustic and supersonic or ultrasound technologies, are known and provide the advantage of allowing the system of the present invention to be entirely leadless.

The system of the present invention further comprises a sensing stent. In use, the sensing stent is located in the coronary sinus of the subject, most preferably in a proximal region of the coronary sinus, more preferably at or close to the origin or ostium of the coronary sinus. The sensing stent is arranged to sense signals from the heart tissue, in particular to sense signals from the atria and/or the ventricles of the heart. The location of the sensing stent in the coronary sinus is particularly advantageous as it allows for the sensing of both atrial and ventricular signals, which is of particular use when coordinating the pacing of both ventricles of the heart.

The sensing stent is operable to sense electrical activity of the heart and receive signals from the heart, in particular to sense both atrial and ventricular activity of the heart, as noted above. In the system of the present invention, the sensing stent does not provide any stimulation to the heart tissue. Rather, the sensing stent provides signal data relating to signals received from the heart for operation and control of other stimulation stents to provide electrical stimulation to the heart tissue, as described hereinbelow.

The sensing stent comprises a stent body. Suitable arrangements for the stent body are known, in particular in relation to angioplasty stents. The sensing stent may be implanted in the coronary sinus vein using known techniques, for example a conventional delivery system comprising a standard coronary sinus sheath, an angioplasty balloon and a lead wire, and arrangements of stent bodies for use with an angioplasty balloon are known in the art. The stent body supports the components of the sensing stent to provide for the sensing function and means for communicating with the controller.

The positioning of the sensing stent in the coronary sinus, in particular in the preferred embodiment within the proximal region of the coronary sinus, provides the sensing stent with a number of distinctive features. First, the stent is located to sense both atrial and ventricular signals. Further, the relatively large internal diameter of the coronary sinus allows the sensing stent to be significantly larger in size than known coronary stents. This in turn allows the sensing stent to comprise such components as larger batteries than known stents, in turn increasing the useable life of the stent. More importantly, the larger permitted diameter of the sensing stent allows the flow of blood through the coronary sinus to the right atrium to be maintained without obstruction. The occlusion of smaller veins by stents is not necessarily a significant problem, as collateral blood vessels will develop. However, as the coronary sinus is the main drainage conduit for venous blood from the heart, it is important to avoid occlusion of the coronary sinus. To this end, the sensing stent is provided with one or more openings or bores therethrough, permitting the passage of blood through or past the sensing stent.

In particular, the sensing stent further comprises a transmitter for sending signals to the controller and one or more electrodes for contacting the tissue of the coronary sinus and detecting electrical signals from the atria and/or ventricles of the heart.

The transmitter may be any suitable transmitter for communicating with the controller. The type and construction of the transmitter will depend upon the nature of the connection to the controller, discussed in more detail below. Suitable transmitters include radio frequency (RF) transmitters for the remote communication with the controller.

The sensing stent further comprises one or more electrodes for sensing the electrical activity of the atria and ventricles of the heart. In use, the electrodes are in contact with the inner wall of the coronary sinus. Suitable electrode configurations are known in the art. The electrodes are disposed to sense both the atrial and ventricular signals detectable from within the coronary sinus. This may be achieved through contact between the one or more electrodes and the inner wall of the coronary sinus. The electrodes may extend into the wall of the coronary sinus, as is known with some designs. However, this is not required in the present invention.

The electrodes may be formed from any electrically conductive material, in particular metal, able to receive electrical signals from the heart tissue of and around the coronary sinus. Suitable forms for the electrodes are known in the art.

The sensing stent may be connected to the controller by means of a lead. In this case, power may be provided to the sensing stent and signals transmitted from the sensing stent by way of the lead. However, as indicated above, it is preferred that the sensing stent is leadless and communicates with the controller remotely. Having the sensing stent and the controller coupled remotely without the use of leads allows the controller to be positioned in an optimum subcutaneous position, for example lower in the chest, on the rib cage or in the lower axillary area in closer proximity to the heart.

In embodiments in which the communication is remote, the system comprises means for remotely powering the sensing stent. In one preferred embodiment, the sensing stent comprises a means for storing electrical power, in particular a battery. Alternatively, the sensing stent may be powered remotely, for example by induction. In such cases, the stent comprises an induction coil for generating an electrical current under the action of an applied magnetic field, as is known in the art. If induction coupling is to be employed, the controller will be in closer proximity to the sensing stent, compared with coupling by way of a lead, which allows the controller to be disposed further from the sensing stent.

Further, in embodiments in which the sensing stent is leadless, the transmitter of the stent is arranged for the remote transmission of data signals to the controller, for example by way of an antenna to transmit radio frequency signals.

In one embodiment, the stent body of the sensing stent is expandable, as is known in the art, and is capable of being moved between a contracted condition and an expanded position. With the stent body in the retracted condition, the stent may be inserted into the subject and implanted in the coronary sinus in known manner, for example using an angioplasty wire and an angioplasty balloon. Such techniques are known for the implanting of stents for coronary or peripheral vessels angioplasty. Expansion of the stent body into the expanded condition urges the sensing electrodes of the stent into contact with the wall of the blood vessel.

In some preferred embodiments, the electrodes of the sensing stent and, optionally other components of the stent, such as the transmitter and power source are held within an assembly, for example within a housing. The housing may be a rigid housing, moved by the stent body. Alternatively, the housing may be flexible, for example arranged to be expanded as the stent body is moved to the expanded condition during insertion. In one arrangement, the assembly is a fixed arrangement and mounted on the outer surface of the stent body. Expansion of the stent body urges the assembly radially outwards within the coronary sinus and into contact with the vessel wall. The assembly may comprise a single unit urged radially outwards in one direction from the stent body. In this arrangement, correct insertion of the stent includes orientation of the stent to place the assembly in contact with the appropriate portion of the wall of the coronary sinus. Alternatively, an assembly of the components may be mounted on two or more opposing sides of the stent body, again being urged radially outwards as the stent body is expanded. The stent body may be expanded using known techniques, as indicated, for example a known angioplasty balloon. This technique employs a pressurised fluid to inflate the balloon within the stent body and thus expand the body radially outwards.

In general, simple contact between the electrodes of the sensing stent and the wall of the coronary sinus is sufficient to allow cardiac signals to be received. However, in some cases, appropriate orientation of the sensing stent within the coronary sinus may improve the reception of signals from the heart and/or the remote transmission of signal data to the controller, for example when using radio frequency transmission or the like.

The system of the present invention further comprises one or more stimulation stents, operable to provide stimulation to a region of the heart of the subject. The or each stimulation stent comprises a receiver for receiving a signal from the controller and one or more electrodes which, when activated, provide electrical stimulation to the heart in accordance with signals received from the controller. The precise number and location of the stimulation stents will vary according to the nature of the cardiac therapy to be provided to the subject and the condition of the subject's heart. Different embodiments of the system in use and the position and number of stimulation stents are discussed in more detail below.

Each stimulation stent comprises a stent body. Suitable arrangements for the stent body are known, in particular in relation to angioplasty stents. The stimulation stent may be implanted in the vein using known techniques, for example a conventional angioplasty balloon and arrangements of stent bodies for use with an angioplasty balloon are known in the art. The stimulation stent comprises one or more electrodes for providing electrical stimulation to the heart tissue in response to signals received from the controller. For receiving signals from the controller, the stimulation stent further comprises a receiver.

The stimulation stent may be connected to the controller by means of a lead. In this case, power may be provided to the stimulation stent and signals transmitted to the stent by way of the lead. However, as indicated above, it is preferred that the stimulation stent is leadless and communicates with the controller remotely. This is particularly preferred for those stimulation stents to be implanted at the more distal locations, which are typically the smaller veins in and around the heart. In embodiments in which the communication is remote, the system comprises means for remotely powering each stimulation stent.

In embodiments in which the system comprises more than one stimulation stent, the system may be arranged to provide stimulation to the heart at multiple sites simultaneously, that is by having the controller activate all the stimulation stents to provide stimulation at their respective target site at the same time. Alternatively, the system may be arranged for stimulation at each of the sites of the stimulation stents with predetermined time delays, in order to provide for optimum resynchronisation of the heart function.

In one embodiment, the stimulation stent comprises a means for storing electrical power, in particular a battery. Alternatively, one or more stimulation stents may be powered remotely, for example by induction. In these embodiments, the stimulation stent may be provided with one or more induction coils to generate an electrical current when a magnetic field is applied. Such techniques for the remote powering of an implanted stent by induction are known in the art.

Further, in embodiments in which the stimulation stent is leadless, the receiver of the stent is arranged for the reception of the remote transmission of data signals from the controller, for example by way of an antenna to receive radio frequency signals.

In one embodiment, the stent body of the stimulation stent is expandable, as is, known in the art, and is capable of being moved from a contracted condition and an expanded position. With the stent body in the retracted condition, the stent may be inserted into the subject and implanted in the target vein in known manner, for example using an angioplasty wire and an angioplasty balloon. Such techniques are known for the implanting of stents for coronary angioplasty. Expansion of the stent body into the expanded condition urges the electrodes of the stent into contact with the wall of the blood vessel, which is located epicardially, on the heart surface, allowing the electrical stimulation to occur.

In some preferred embodiments, the stent electrodes and, optionally other components of the stent, such as the receiver and power source are held within an assembly, for example within a housing. The housing may be a rigid housing, moved by the stent body. Alternatively, the housing may be flexible, for example arranged to be expanded as the stent body is moved to the expanded condition during insertion. In one arrangement, the assembly is a fixed arrangement and mounted on the outer surface of the stent body. Expansion of the stent body urges the assembly radially outwards within the target vein. The assembly may comprise a single unit urged radially outwards in one direction from the stent body. In this arrangement, correct insertion of the stent includes orientation of the stent to place the assembly in contact with the appropriate portion of the vessel wall, for example the epicardial side of the target coronary sinus vein. Alternatively, an assembly of the components may be mounted on two or more opposing sides of the stent body, again being urged radially outwards as the stent body is expanded. The stent body may be expanded using known techniques, as indicated, for example a known angioplasty balloon. This technique employs a pressurised fluid to inflate the balloon within the stent body and thus expand the body radially outwards. As an alternative, the stent may be expanded using a standard pacing lead with a cam mechanism at the distal end, which is attached to the stented electrode housing, similar to the technology currently used for deployment of active fixation leads, but with the active mechanism deploying the stent body within the target vein.

In a further embodiment, the stimulation stent comprises a stent body. The stent body is expandable as described hereinbefore, in order to secure the stent within the target vein. Further components of the stent, such as the receiver, power source, antenna, are mounted to the stent body. In one preferred arrangement, these further components are retained within a housing held at one end of the stent body. One or more electrodes for providing electrical stimulation to, the heart are provided in an electrode assembly extending from the stent body, for example in which the one or more electrodes are mounted on a multipole lead, similar to the distal end of a standard multipole pacing lead extending from the stent body or housing. The electrode assembly may have any suitable length, as required to reach the target site for stimulation. A length of from 10 to 50 mm is suitable in many embodiments, to accommodate a range of distal vein sizes. It is particularly preferred that the diameter of the electrode assembly is smaller than the diameter of the stent body.

This arrangement is advantageous for implanting the stimulation stent in small target veins, typically the most distal veins to be reached. In particular, the arrangement allows for the stent body and the further aforementioned components in a proximal position relative to the target site for stimulation, especially in a proximal portion of the vein that is larger in diameter and easier to access. This allows the stent body and the further components to be of a larger size, and thus easier to implant and handle. The electrodes are disposed in the smaller electrode assembly distally of the stent body and can extend into the narrower, more distal portions of the vein. This arrangement provides for the secure and accurate placement of a stimulation stent and provides for more accurate pacing and stimulation of the heart, for example avoiding the unwanted stimulation of surrounding organs or tissue, such as the diaphragm.

Accordingly, in a further aspect, the present invention provides a stent assembly for providing stimulation to a target site of a target blood vessel within the heart of a subject, the diameter of the target blood vessel at the target site being less than the diameter of the target blood vessel at a position proximal to the target site, the assembly comprising:

a stent body of a size to be implanted and retained in the position proximal to the target site; and an electrode assembly arranged to extend longitudinally from the stent body within the target blood vessel in a distal direction from the proximal position to the target site to be stimulated.

As described above, the stents of the system of the present invention, including both the sensing stent and the one or more stimulation stents, may be implanted using known techniques, in particular over the wire techniques currently employed in angioplasty.

The system of the present invention is particularly advantageous in allowing a plurality of stimulation stents to be deployed at multiple sites in the heart of the subject. In particular, by having the stimulation stents leadless and communicating remotely with the controller, it is possible to provide multisite stimulation to the left ventricle of the heart.

According to a further aspect of the present invention, there is provided a system for the multisite artificial stimulation of the left ventricle of the heart of a subject, the system comprising:

a controller;

a sensing stent for location in the coronary sinus of the subject, the sensing stent comprising a sensing assembly for sensing atrial and/or ventricular signals from the heart of the subject and a transmitting assembly for transmitting signal data to the controller; and a plurality of stimulation stents, each stimulation stent for location in a vein of the subject distal of the sensing stent for providing multisite stimulation to the left ventricle of the heart, each stimulation stent comprising a receiver for receiving signal data from the controller and a electrode assembly for providing a stimulating electrical signal to the heart of the subject.

The system may be arranged and implanted in the subject as described above. In one method of implantation, the coronary sinus is intubated with a delivery sheath, facilitating the delivery of stents to target sites in the veins of the heart. Once the delivery sheath is in place, the stimulation stents are first placed in the left ventricular target veins of the coronary sinus for stimulation of the left ventricle and, if required, in the small cardiac vein for stimulation of the right ventricle. Thereafter, if required, a further stent may be placed in a distal position in the coronary sinus for atrial pacing. Finally, the sensing stent is placed at the proximal location in the coronary sinus, as described above.

The system of the present invention may be operated to allow the intrinsic activity of the right ventricle to be sensed and determine the optimal left ventricular synchronization timing, without the need for automatic right ventricular stimulation, providing that no advanced atrioventricular block is present in the subject. Suitable algorithms for this form of pacing of the heart are known in the art and are currently used to maximise the percentage of cardiac resynchronization therapy in patients with atrial fibrillation.

The system of the present invention is particularly suitable for performing cardiac resynchronisation therapy (CRT) to the heart of the subject, by way of the multisite stimulation of the left ventricle and stimulation of the right ventricle, thereby synchronising ventricular action.

Therefore, according to a further aspect of the present invention, there is provided a system for the biventricular stimulation of the heart of a subject, the system comprising:

a controller;

a sensing stent for location in the coronary sinus of the subject, the sensing stent comprising a sensing assembly for sensing atrial and/or ventricular signals from the heart of the subject and a transmitting assembly for transmitting signal data to the controller; and a plurality of stimulation stents, each stimulation stent for location in a vein of the heart distal of the sensing stent for providing multisite stimulation to the left ventricle of the heart;

a stimulation stent for location in a vein of the heart distal of the sensing stent, for providing stimulation to the right ventricle of the heart;

each stimulation stent comprising a receiver for receiving signal data from the controller and a electrode assembly for providing a stimulating electrical signal to the heart of the subject;

in use the system synchronising the action of the ventricles of the heart.

As noted above, the sensing stent is preferably arranged to be located in the proximal region of the coronary sinus. The stimulation stent for location to provide stimulation to the right ventricle is preferably arranged to be disposed in the ventricular branch of the small cardiac vein or in the middle cardiac vein on the undersurface of the heart. One or more stimulation stents may be provided to stimulate the left ventricle. In particular, stimulation may be applied to tissue from a stent within one or more veins extending from the coronary sinus to the left ventricle, especially by way of a stent implanted in one or more of the posterior-lateral cardiac vein, the middle cardiac vein and the lateral cardiac vein.

One or more of the stents may be provided with means for storing one or more active ingredients for dispensing to the tissue of the subject and means for dispensing the active ingredient. For example, in use, the contact between one or more of the stents in the system and the tissue of the blood vessel in which the stent is positioned may give rise to inflammation at the electrode/tissue interface. This may in turn affect the stimulation or sensing functions of the stents. Accordingly, in one embodiment, one or more of the stents may be provided with means for storing and eluting in a controlled manner one or more steroids, in order to control or eliminate localised tissue inflammation.

The present invention also relates to methods for providing cardiac therapies to a subject.

In a further aspect, the present invention provides a method for providing stimulation to the heart of a subject, the method comprising:

sensing electrical activity of the heart at a location in the proximal region of the coronary sinus using a sensing stent implanted in the coronary sinus;

transmitting first signal data from the proximal region of the coronary sinus to a controller;

generating second signal data for providing electrical stimulation to target tissue of the heart in response to the signal data received from the proximal region of the coronary sinus;

transmitting the second signal data to an stimulation stent for stimulation of the target tissue; and providing electrical stimulation to the target tissue of the heart in response to the second signal data.

The method of the present invention may be employed in pacing one or more regions of the heart of the subject. The method may also be applied in synchronising activity of the heart, in particular in providing cardiac resynchronisation therapy (CRT) to the heart.

The method of the present invention senses activity of the heart of the subject at a location in the proximal region of the coronary sinus, in particular in the portion of the coronary sinus at or adjacent its origin. In one embodiment, the sensing stent is located in the coronary sinus proximal of the oblique vein, more preferably in the coronary sinus between its junctions with the oblique vein and the middle cardiac vein. By conducting the sensing step of the method at this location, signals of both the atrial and ventricular activity of the heart are sensed. Further, the larger size of the coronary sinus vein allows for a larger design of the sensing stent, with advantages in its construction, implantation and operation, as discussed above.

In normal operation of the heart, pacing of the heart is controlled by cells at the sinus or sinoatrial node in the right atrium of the heart. The sinus node generates the sinus rhythm followed by the heart tissue. In subjects in which the sinus node is intact and functioning properly, it is sufficient that signals from the right atrium of the heart are sensed. This can be achieved, by conducting the sensing step at the proximal region of the coronary sinus. However, in subjects in which the function of the sinus node is impaired, sensing at the proximal region of the coronary sinus allows for both atrial and ventricular activity of the heart to be sensed using a single sensing stent implanted at this location.

In the method, the sensing step conducted at the coronary sinus generates a set of first signal data. The first signal data are transmitted from the coronary sinus to a remote controller, as described hereinbefore. The first signal data are used to generate a set of second signal data, which are transmitted to one or more stimulation stents. The stimulation stents are located at sites in the heart appropriate to providing the required stimulation, in particular tributary veins of the coronary sinus. The stimulation stents respond to the received second signal data and provide electrical stimulation to the heart tissue in response thereto.

It is particularly preferred that signal data are transmitted between the sensing stent in the coronary sinus, the controller, and the one or more stimulation stents, remotely, that is without the use of leads. Such remote communication may be achieved in known manner, for example using radio frequencies. Suitable frequencies approved for medical applications are known in the art.

In one embodiment, the method provides stimulation to the tissue of the heart at one location, that is unisite pacing. For example, unisite pacing may be applied using the method of the present invention to the left atrium or, more preferably, one of the ventricles of the heart, or both the left atrium and a ventricle for patients with a conventional bradycardia pacing indication. However, the method of the present invention is particularly suitable and advantageously applied in the stimulation of multiple sites within the heart of the subject. The present invention is particularly suitable and advantageous when applied in the multisite pacing of the left ventricle, in particular to provide intraventricular resynchronisation.

In one embodiment, the method is used to provide atrial pacing, in particular by stimulating the left atrium using a stimulation stent disposed in the coronary sinus at a location distal of the sensing stent, in particular at or adjacent the junction between the coronary sinus and the great cardiac vein or even more distally in the great cardiac vein. The stimulation stent in the distal region of the coronary sinus may be used to provide pacing of the left atrium, where necessary in response to atrial sensing from the sensing stent, for example where the sinus rate would be too slow as a result of medication.

Similarly, the method may be used to applying unisite or multisite pacing to one of both of the left or right ventricles.

Thus, in a further embodiment, the method provides stimulation to one or both ventricles of the heart of the subject. For example, in the case of applying pacing to the left ventricle, stimulation may be applied to tissue from a stent within one or more veins extending from the coronary sinus to the left ventricle. In particular, pacing may be applied to the left ventricle by way of a stent implanted in one or more of the posterior-lateral cardiac vein, the middle cardiac vein and the lateral cardiac vein.

The number of sites employed to provide pacing to the left ventricle may depend upon such factors as the condition of the veins in the heart of the subject and the nature of the therapy to be provided. In the majority of subjects, more than one vein will be available for receiving a stimulation stent, thereby allowing multisite pacing of the left ventricle to occur. In some subjects, one, typically a larger, vein may only be available to receive a stimulation stent, in turn allowing only unisite pacing of the left ventricle. In such cases, the resulting pacing treatment is equivalent in effect to the current unisite left ventricle pacing practices known in the art.

Similarly, when applying pacing to the right ventricle, stimulation may be applied to the heart tissue by means of a stent implanted within one or more veins extending from the coronary sinus to the right ventricle, for example the ventricular branch of the small cardiac vein, or indeed the middle cardiac vein running between the ventricles. Single site pacing of the right ventricle is preferred. In many cases, the right ventricle of the subject retains its normal size and function. In such cases, it is often sufficient to provide pacing to the right ventricle, which may be achieved using stimulation at a single site. Right ventricular failure is uncommon and associated with a pathology that is not prone to responding to CRT. Further, in practice, stimulation sites for the right ventricle, apart from the small cardiac vein or middle cardiac vein, are not readily accessible without using leads extending into the ventricle itself.

In contrast, the left ventricle is predominantly affected in subjects with congestive heart failure. In particular, the left ventricle becomes dilated and dyssynchronous. For these reasons, the left ventricle is often very responsive to both interventricular resynchronisation (CRT) and intraventricular resynchronisation by way of multisite pacing. The number of stimulation sites, and hence the number of stimulation stents, used in the multisite stimulation of the left ventricle will depend upon the condition of the subject and the number of target veins accessible.

In a further embodiment of the method of the present invention, anti-bradycardia pacing is applied to the heart, in particular using the sensing stent in the proximal coronary sinus for atrial and ventricular sensing, a first stimulation stent in the distal coronary sinus for atrial pacing and a second stimulation stent in a ventricular branch of the small or in the middle cardiac vein for sequential pacing of the right ventricle.

In a still further embodiment, the method of the present invention is used to provide multisite pacing to the ventricles of the heart of the subject, especially cardiac resynchronisation therapy (CRT), in particular pacing to both the right and left ventricles at the same time, so-called 'biventricular pacing', thereby synchronising the action of the ventricles. Currently, when using known lead-based pacing systems, it is generally possible to use one pacing site for the left ventricle located in a suitable vein leading from the coronary sinus. It is an advantage of the present invention that multisite pacing of the left ventricle may be achieved, in particular when leadless communication between the controller and the stimulation stents is used. Such multisite pacing of the left ventricle provides an improved cardiac resynchronisation therapy.

Accordingly, in a further aspect, the present invention provides a method for the biventricular pacing of the heart of a subject, the method comprising:

sensing electrical activity of the heart at a location in the proximal region of the coronary sinus using a sensing stent implanted in the coronary sinus;

transmitting first signal data from the proximal region of the coronary sinus to a controller;

generating second signal data for providing electrical stimulation to target tissue of the heart in response to the signal data received from the proximal region of the coronary sinus;

transmitting the second signal data to a plurality of stimulation stents disposed for multisite stimulation of the left ventricle and an stimulation stent disposed for stimulation of the right ventricle; and providing electrical stimulation to both the left and right ventricles in response to the second signal data.

Alternative embodiments of the present invention provide multisite, leadless pacing of the left ventricle, as described hereinbefore, in conjunction with standard lead based stimulation for pacing each of the right atrium and the right ventricle. These embodiments are particularly useful for subjects where having one or two leads extending to sites in the right side of the heart is acceptable and where single site pacing of the left ventricle, for example for the purpose of performing more basic cardiac resynchronisation therapy, would be sufficient. An example would be the case of a very frail subject suffering from end stage heart failure, where the risks of a more prolonged procedure may be even more considerable. Another example would be of patients with existing and longstanding right sided leads who would benefit from an upgrade to a CRT pacing system, for example if the function of the left ventricle has deteriorated as a result of pacing of the right ventricle alone. The latter artificially induces LBBB, which is related to right ventricle pacing.

Embodiments of the present invention will now be described, by way of example only, having reference to the accompanying drawings, in which:

FIG. 3a is a side elevational view of a stimulation stent according to one embodiment of the present invention;

FIG. 3b is a perspective view of the electrode housing of the stent of FIG. 3a;

Figure 1A:
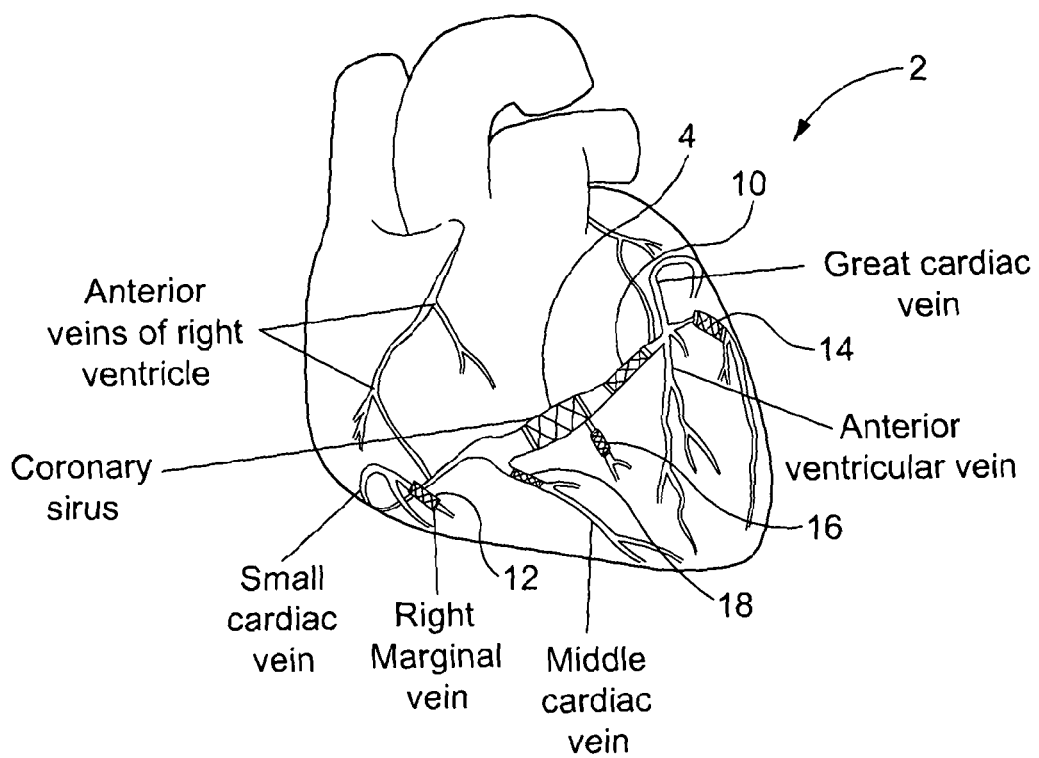
FIG. 1a is a first perspective view of the exterior of a heart showing the general arrangement of veins.
Figure 1B:
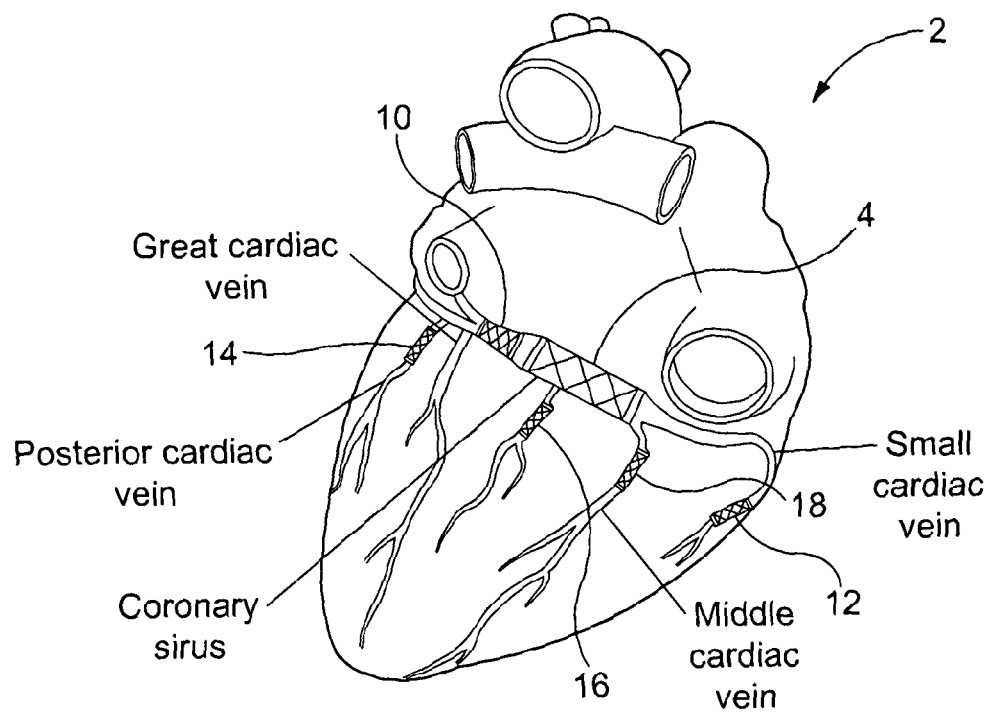
FIG. 1b is a second perspective view of the exterior of a heart showing the general arrangement of veins.

Referring to FIGS. 1a and 1b, there is shown in each figure a perspective view of the exterior of a human heart, generally indicated as 2. Indicated on the heart 2 and labelled are the major veins of the heart, in particular the coronary sinus and the tributary veins extending therefrom to the left and right ventricles. The arrangement of the veins is shown in more detail in FIG. 2. In particular, FIGS. 1 and 2 show the coronary sinus and the arrangement of various tributary veins thereof, including the small cardiac vein, the middle cardiac vein, the oblique vein, the posterior cardiac vein and the great cardiac vein.

Figure 2:
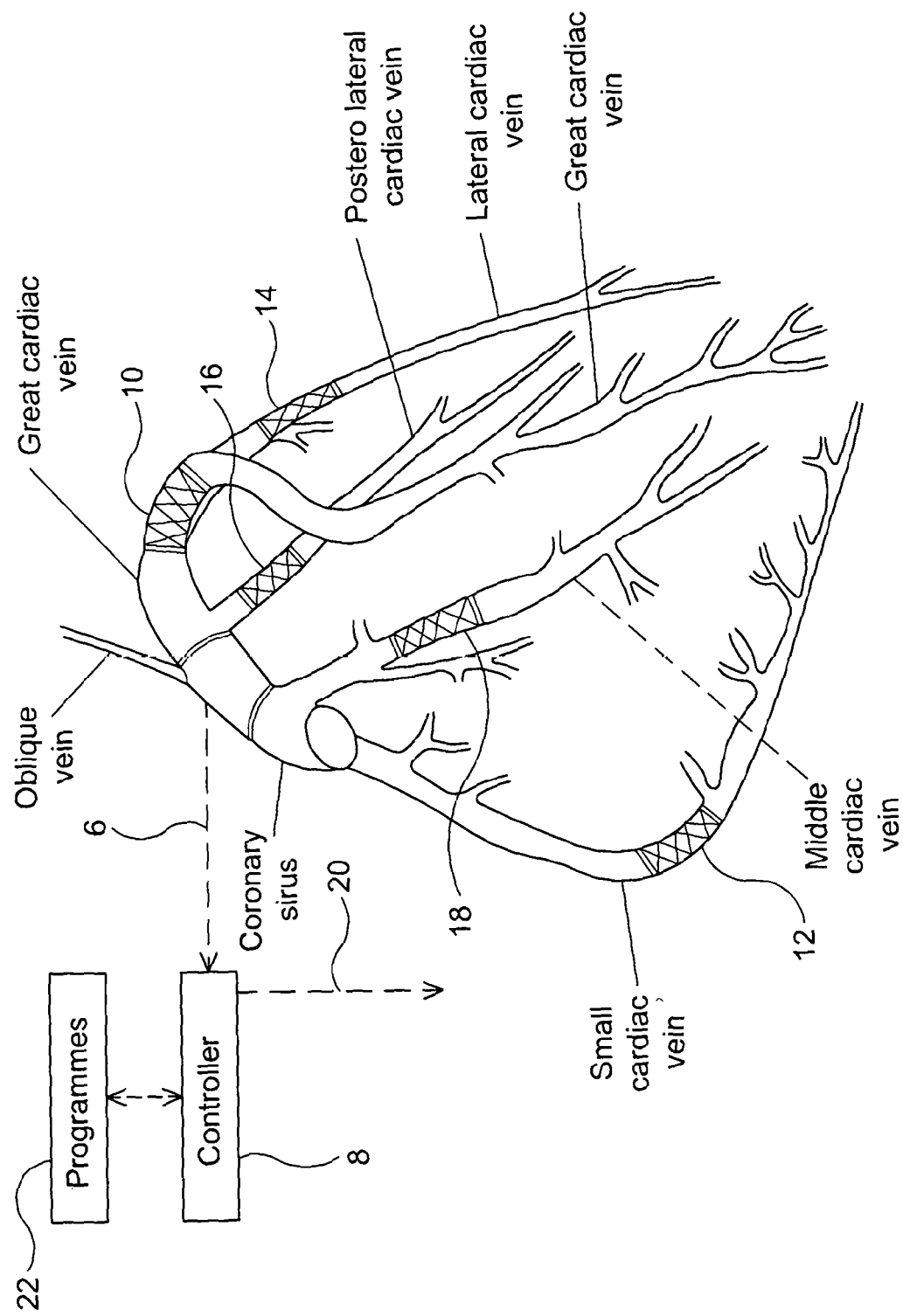
FIG. 2 is a diagrammatical representation of the major veins of the heart and showing the placement of stents according to one embodiment of the present invention.

FIGS. 1 and 2 further show the placement of a system for providing artificial stimulation to tissue of the heart according to one embodiment of the present invention.

The system comprises a sensing stent 4 positioned in a proximal position in the coronary sinus, in particular in the region of the origin of the coronary sinus between the oblique vein and the middle cardiac vein. The sensing stent 4 is a leadless stent implanted in the coronary sinus. The sensing stent 4 functions to sense both atrial and ventricular signals from the electrical activity of the heart and transmit radio frequency data signals 6 to a controller 8 shown in FIG. 2.

The controller 8 has a processor programmed with appropriate software for processing radio frequency signals. Such processing techniques are known in the art and used in existing pacemaker systems. In order to overcome potential issues arising from distance adversely affecting induction coupling transmission, the controller 8 can be placed in a lower chest position in closer proximity to the heart 2. By having no leads attached, the implantation procedure for the controller is simplified, as there is no need to tunnel any hardware subcutaneously, therefore making the implant procedure straightforward.

The controller 8 is programmed and data regarding the performance of the system and the subject exported by means of remote radio frequency communication with a programmer 22.

The system further comprises a plurality of stimulation stents disposed distally of the sensing stent 4 and arranged within veins of the heart as follows:

A first stimulation stent 10 is disposed at the junction between the coronary sinus and the great cardiac vein and is operable to provide stimulation and pacing to the left atrium. In use, the first stimulation stent 10 provides unisite pacing to the left atrium.

A second stimulation stent 12 is disposed within a ventricular branch of the small cardiac vein or in the middle cardiac vein (as illustrated by stent 18) and is operable to provide stimulation and pacing to the right ventricle. In use, the second stimulation stent 12 or 18 provides unisite pacing to the right ventricle.

The system comprises one to three further stimulation stents to provide multisite pacing of the left ventricle, as follows. As shown in FIG. 2, a third stimulation stent 14 is disposed within the lateral cardiac vein; a fourth stimulation stent 16 is disposed within the posterio-lateral cardiac vein; and a fifth stimulation stent 18 is provided within the middle cardiac vein. The stimulation stent 18, in view of its location, is capable of providing stimulation to either the left or right ventricles.

The precise location of the stents within the subject is determined by a range of factors. For example, positioning of a stent will depend upon the size of the target blood vessel. The size of blood vessels will vary from subject to subject, depending upon their age, size and condition. Further, in general, there can be significant differences in the physiology of subjects, for example in the number and size of veins around the heart. These differences lead to differences in the final placement of the stents of the system. Further factors affecting the positioning of the stents include the quality of the electrical signals received from the heart and/or provided to the heart.

Preferably, the stimulation stents are positioned with a sufficient distance between adjacent stents to ensure that different regions of the heart are being stimulated, rather than multiple stimulation of a single site.

Further, it is an advantage of the system of the present invention that the stimulating stents may be located at proximal to mid-vessel positions, compared with stimulating stents of known systems. This in turn allows the stimulating stents to provide stimulation at optimal sites and avoid stimulation of the phrenic nerve.

The sensing stent is implanted in the coronary sinus using known techniques applied to angioplasty or coronary artery stents, in particular using an angioplasty wire and an angioplasty balloon of appropriate size to expand the stents at the desired location. Apparatus and techniques for the insertion of stents in this manner are known in the art. The coronary sinus is conventionally accessed through the right atrium which is most commonly approached through the left venous system at left subclavian vein level. However, the stents could also be delivered via the right femoral vein approach using delivery systems similar to the ones currently used in electrophysiological studies and known in the art. The stimulation stents are implanted in like manner at the location in their respective veins. When implanting the stents of the system, the distally disposed stents are implanted first, with the proximal stents being implanted thereafter, in particular the sensing stent being implanted last.

In particular, the stimulation stents are each delivered via the coronary sinus using a known coronary sinus sheath and a standard 0.014" guide wire. For placement of the stent 12 for stimulation of the right ventricle, the pacing site is accessed via either the small cardiac vein between the right atrium and the right ventricle (as shown in the Figures) or a suitable branch of the middle cardiac vein between the right ventricle and the left ventricle. The decision regarding the best position for the stimulation stent 12 is determined by the implanter and is based on determining the size and anatomy of the aforementioned veins. In subjects with significant conduction deficit, the stent 12 should be implanted first. Alternatively, a temporary right ventricular apical lead can be implanted for the duration of the procedure and be removed after the electrical parameters of all stents have been checked and found to be satisfactory.

The stimulation stent 10 in the distal portion of the coronary sinus for pacing the left atrium is positioned after the stimulation stents 14, 16, 18 have been placed in the target veins of the left ventricle, but preferably before the stimulation stent 12 in the small cardiac vein and the sensing stent 4 in the coronary sinus are positioned as this regime is easier to achieve.

Once the sensing stents have been deployed and all the sensing and pacing parameters checked, the delivery system is withdrawn from the coronary sinus. As the system is leadless, the implanting of the stents occurs without the current concerns that one or more leads may be inadvertently displaced during the removal of the delivery system.

Each stimulation stent 10-18 comprises one or more pairs of electrodes acting as electrical poles for the provision of electrical stimulation to the surrounding tissue. Pacing impedance and threshold are checked remotely and in turn for every pair of pacing poles present on each stimulation stent during the implant procedure. The position of each stent can be adjusted in the vein to achieve best pacing parameters and avoid inadvertent diaphragmatic pacing before being deployed under pressure in its final position. When more than one stimulation stent is used in order to achieve multisite pacing of the left ventricle, as is the case with the embodiment shown in FIGS. 1 and 2, the stimulation stents 14, 16, 18 are programmed to respond simultaneously to the coordinated pulses generated by the controller following atrial sensing provided by the sensing stent. The pacing stimuli for the left ventricle are generated at the same time as the pacing stimulation for the right ventricle, for optimal re-synchronization of the heart function. However, a small delay between the right ventricle and left ventricle pacing may be programmed if necessary, similar to existing pacemaker programming options.

For subjects in atrial fibrillation, where atrial sensing and pacing are not necessary, the stimulation stents 12-18 for the left ventricle and right ventricle would simply be programmed to pace at a rate responsive rate generated by the pacemaker. During atrial fibrillation, atrial impulses are rapid, typically ranging from 250 to 400 beats per minute. The atrioventricular node limits the number of beats reaching the ventricles. However, this process is variable and can be irregular, giving rise to an erratic heart beat. In general, a slower rate transmitted to the ventricles is better, as it enhances the percentage of cardiac resynchronisation. At higher rates, pacemaking systems are generally inhibited and do not function properly to pace the heart. As a result, the CRT function can be lost. The rate at which pulses are transmitted by the atrioventricular node can be regulated, for example by medication or by techniques such as radio frequency ablation. This can ensure that no pulses are transmitted to the ventricles by the atrioventricular node, in turn allowing the system to provide complete CRT to the heart.

In order to optimize the percentage of cardiac resynchronisation therapy to be applied, a standard atrioventricular node radiofrequency ablation may be necessary, as it would be with the known lead-based systems.

In operation of the system, the controller interprets the received data signals 6 and generates a set of radio frequency stimulation data signals 20, which are transmitted to each stimulation stent 10-18. Each stimulation stent responds to the received signals and provides electrical stimulation to the adjacent tissue of the heart through one or more electrodes.

The system is shown in FIGS. 1 and 2 for providing cardiac resynchronisation therapy (CRT) to the heart, in particular with stimulation and pacing of the right atrium and biventricular pacing of both the left and right ventricles, including multisite pacing of the left ventricle.

Figure 3:
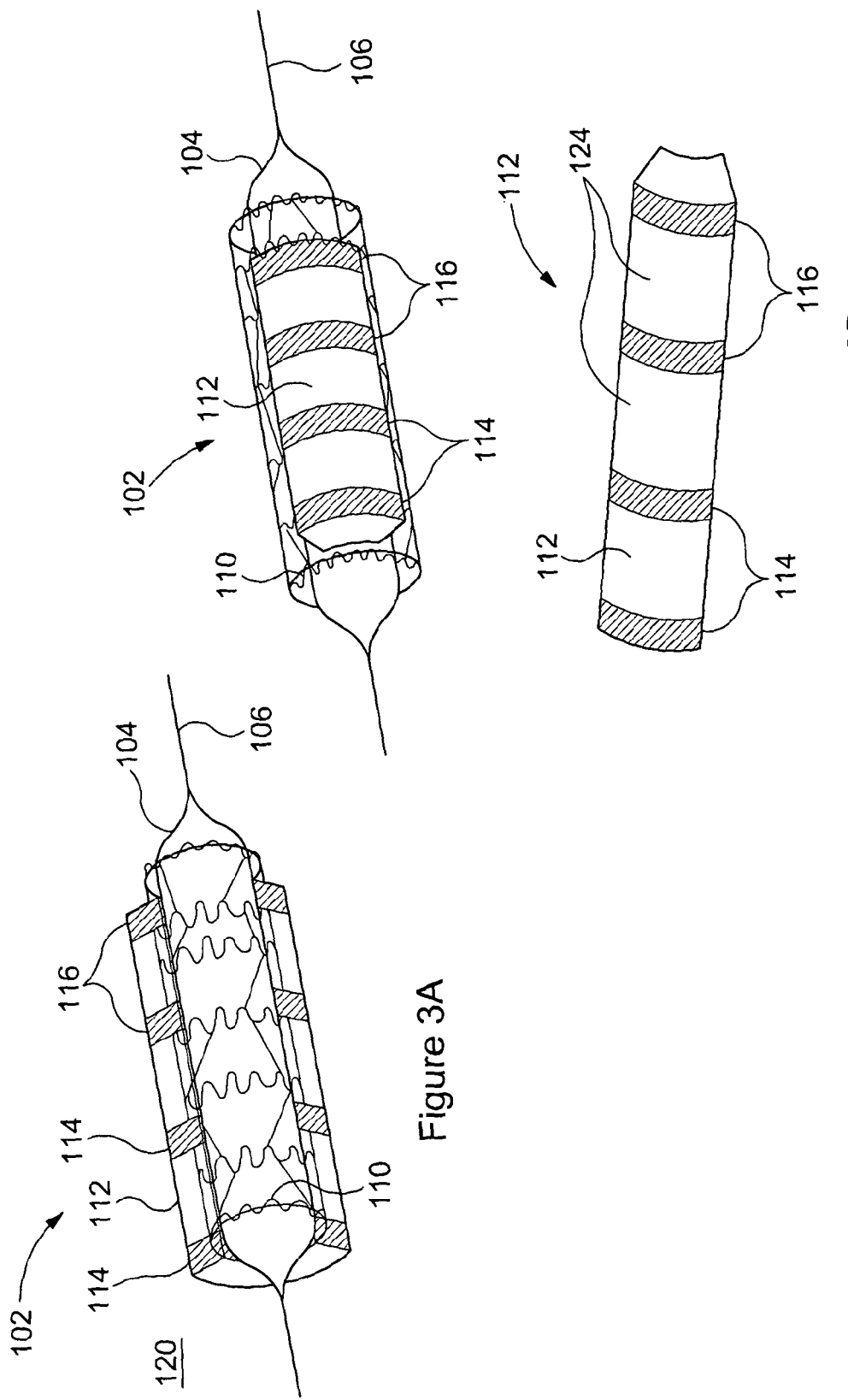

Turning to FIGS. 3a and 3b, there is shown a first embodiment of a stimulation stent, generally indicated as 102. The stent 102 is shown mounted on an angioplasty balloon 104 on a guide wire 106, in known manner, as it would be when being advanced in the target vein.

The stent 102 comprises a generally cylindrical, expandable stent body 110 of known configuration, shown extending around the balloon 104. When being implanted, the stent body 110 is contracted and the balloon 104 deflated. To install the stent 102 at the target location, the balloon 104 is inflated in known manner, in turn expanding the stent body 110 radially outwards and securing the stent within the blood vessel. The balloon 104 and the guidewire 106 are then deflated and removed, again in known manner.

An electrode housing 112 is mounted to one side of the stent body 110 and extends along and radially outwards from the stent body. The electrode housing is generally wedge-shaped in cross-section, as shown more clearly in FIG. 3b, with the narrower portion of the housing adjacent the stent body 110. The housing 112 holds two pairs of electrodes 114, 116. When installed, the expansion of the stent body 110 urges the electrodes 114, 116 radially outwards and into contact with the inner wall of the vein, in turn allowing electrical stimulation to be provided to the surrounding heart tissue 120. The pairs of electrodes allow for different configurations of stimulation to be applied, as necessary. For example, if phrenic nerve stimulation and twitching is encountered with one pattern of stimulation via one configuration of electrodes, a different combination may be used.

The housing 110 contains further components for the operation of the stimulation stent, including an antenna (not shown for clarity) for receiving radio frequency signals from the controller 8, an electrical circuit 122, and requisite capacitors 124. The stent 102 is arranged to be powered by induction coupling, as is known in the art and, as a result, does not have a local power source, such as a battery.

Figure 4:
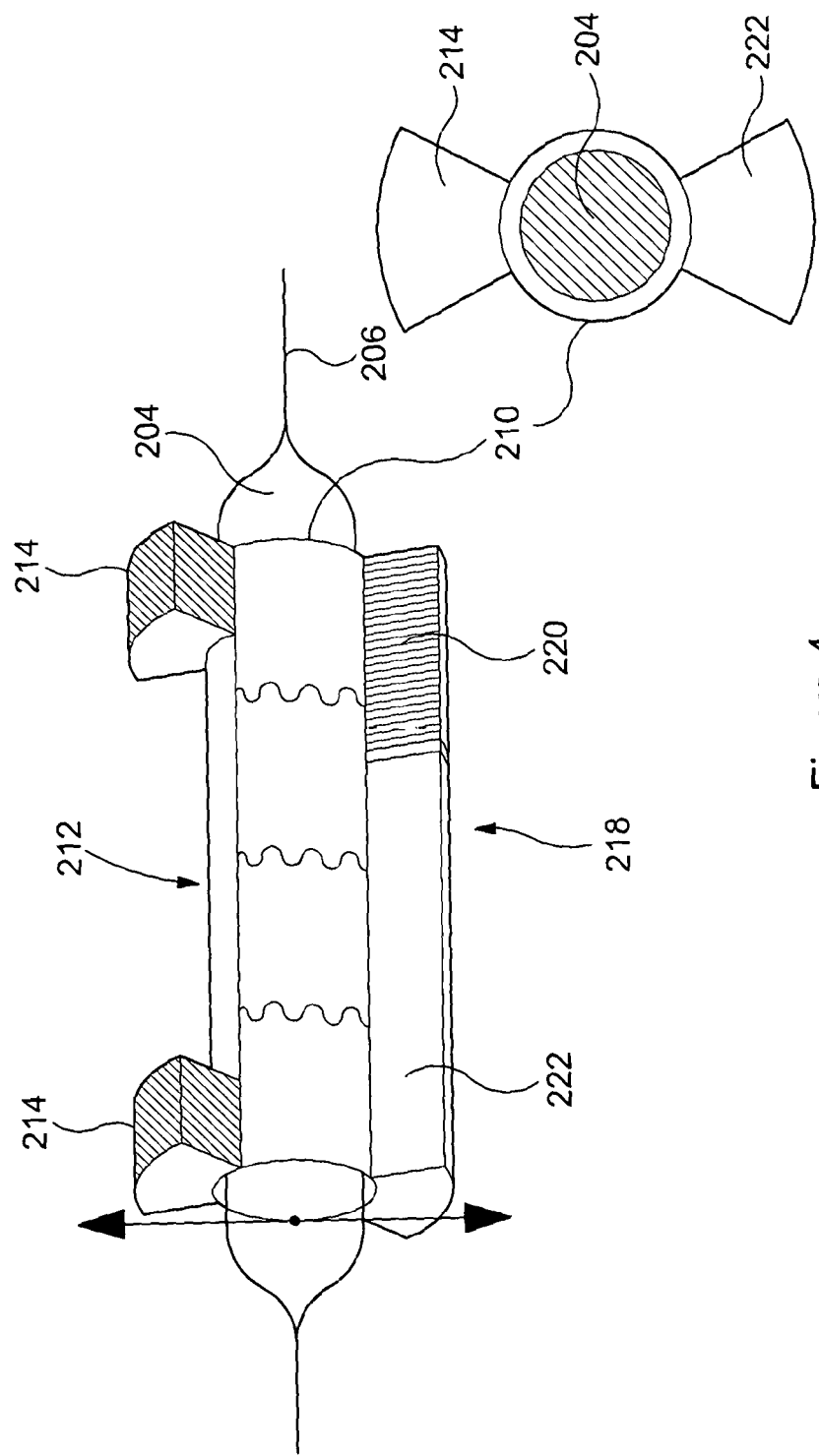
FIG. 4 is a side elevational view of a stimulation stent according to a second embodiment of the present invention.

Turning to FIG. 4, there is shown a second embodiment of a stimulation stent, generally indicated as 202. The stent 202 is shown mounted on an angioplasty balloon 204 on a guide wire 206, in known manner, as it would be when being installed in the target vein.

The stent 202 comprises a generally cylindrical, expandable stent body 210 of known configuration, shown extending around the balloon 204. Installation of the stent is as described above with respect to the embodiment of FIG. 3.

An electrode housing 212 is mounted to one side of the stent body 210 and extends along and radially outwards from one side of the stent body. The housing 212 holds a pair of electrodes 214. When installed, the expansion of the stent body 210 urges the electrodes 214 radially outwards and into contact with the inner wall of the vein, in turn allowing electrical stimulation to be provided to the surrounding heart tissue.

A second housing 218 is disposed on the opposite side of the stent body to the electrode housing 212 and contains further components for the operation of the stimulation stent, including an antenna (not shown for clarity) for receiving radio frequency signals from the controller 8, circuitry 220, and requisite capacitors 222. The stent 202 is arranged to be powered by induction coupling, as is known in the art and, as a result, does not have a local power source, such as a battery. Alternatively, the stent 202 may be provided with a battery located within the housing 212, for example for use with a radio frequency communication system.

Figure 5:
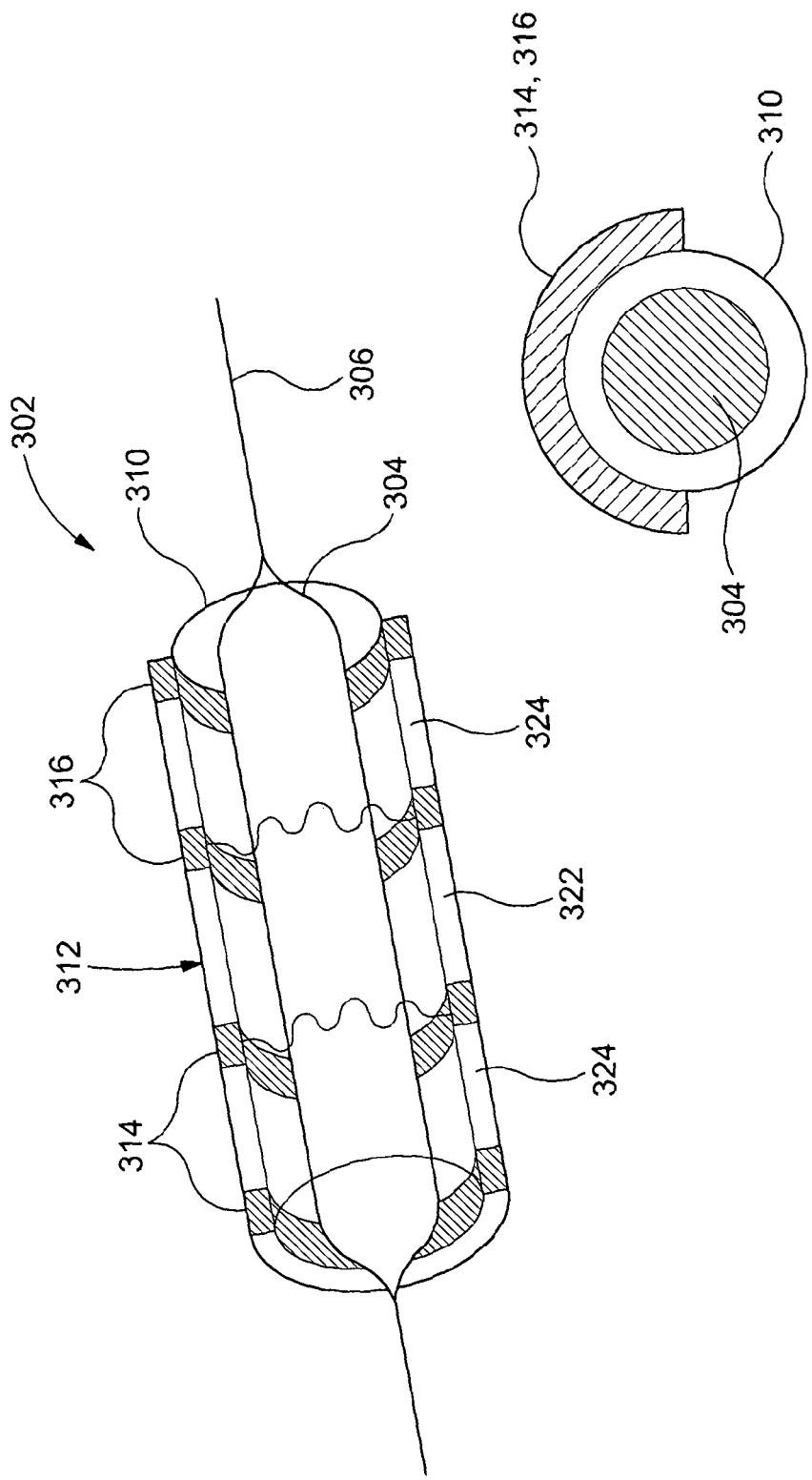
FIG. 5 is a side elevational view of a stimulation stent according to a third embodiment of the present invention.

Turning to FIG. 5, there is shown a third embodiment of a stimulation stent, generally indicated as 302. The stent 302 is shown mounted on an angioplasty balloon 304 on a guide wire 306, in known manner, as it would be when being installed in the target vein.

The stent 302 comprises a generally cylindrical, expandable stent body 310 of known configuration, shown extending around the balloon 304. Installation of the stent is as described above with respect to the embodiment of FIG. 3.

A generally arcuate electrode housing 312 is mounted to one side of the stent body 310 and extends along and radially outwards from one side of the stent body. The housing 312 holds two pairs of electrodes 314, 316. When installed, the expansion of the stent body 310 urges the electrodes 314, 316 radially outwards and into contact with the inner wall of the vein, in turn allowing electrical stimulation to be provided to the surrounding heart tissue. As described above, the pairs of electrodes may be used in different configurations to optimise the stimulation provided to the tissue.

The housing 312 contains further components for the operation of the stimulation stent, including an antenna (not shown for clarity) for receiving radio frequency signals from the controller 8, an electrical circuit 322, and requisite capacitors 324. The stent 302 is arranged to be powered by induction coupling, as is known in the art and, as a result, does not have a local power source, such as a battery. Alternatively, the stent 302 may be provided with a battery located within the housing 312, for example for use with a radio frequency communication system.

Figure 6:
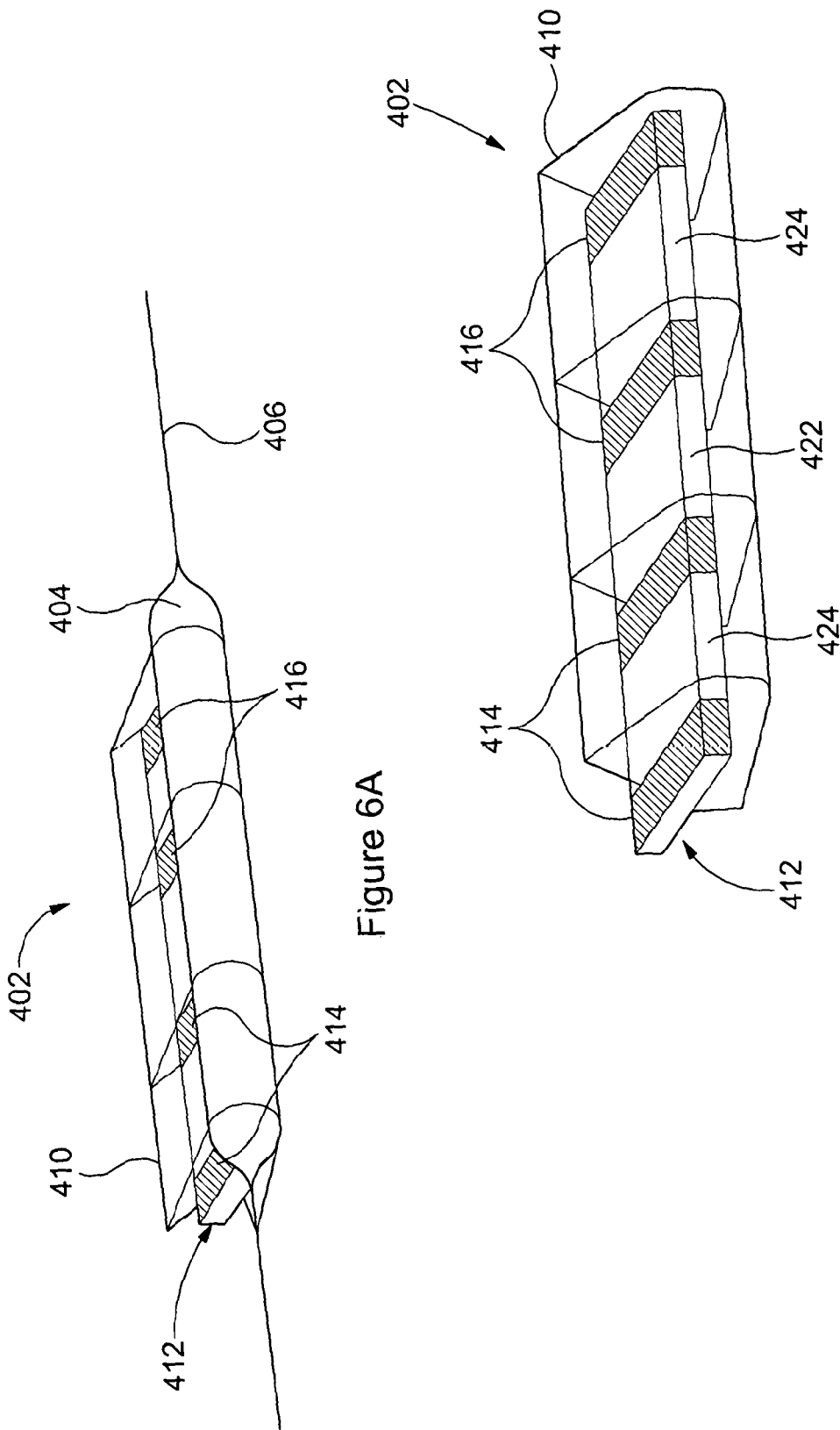
FIG. 6a is a side elevational view of a stimulation stent according to a fourth embodiment of the present invention in a condition to be installed in a larger vein.
FIG. 6b is a side elevational view of the stent of FIG. 6a in a condition when installed in a vein.

Turning to FIGS. 6a and 6b, there is shown a fourth embodiment of a stimulation stent, generally indicated as 402. The stent 402 is shown in FIG. 6a mounted on an angioplasty balloon 404 on a guide wire 406, in known manner, as it would be when being installed in the target vein.

The stent 402 comprises an expandable stent body 410 having a generally rounded triangular cross-section, shown extending at one around the balloon 404. Installation of the stent is as described above with respect to the embodiment of FIG. 3.

An electrode housing 412 is mounted within the stent body 410 and extends along and radially outwards from one side of the stent body. The housing 412 holds two pairs of electrodes 414, 416. When installed, the expansion of the stent body 410 urges the electrodes 414, 416 radially outwards and into contact with the inner wall of the vein, in turn allowing electrical stimulation to be provided to the surrounding heart tissue.

The housing 412 contains further components for the operation of the stimulation stent, including an antenna (not shown for clarity) for receiving radio frequency signals from the controller 8, an electrical circuit 422, and requisite capacitors 424. The stent 402 is arranged to be powered by induction coupling, as is known in the art and, as a result, does not have a local power source, such as a battery.

Figure 7:
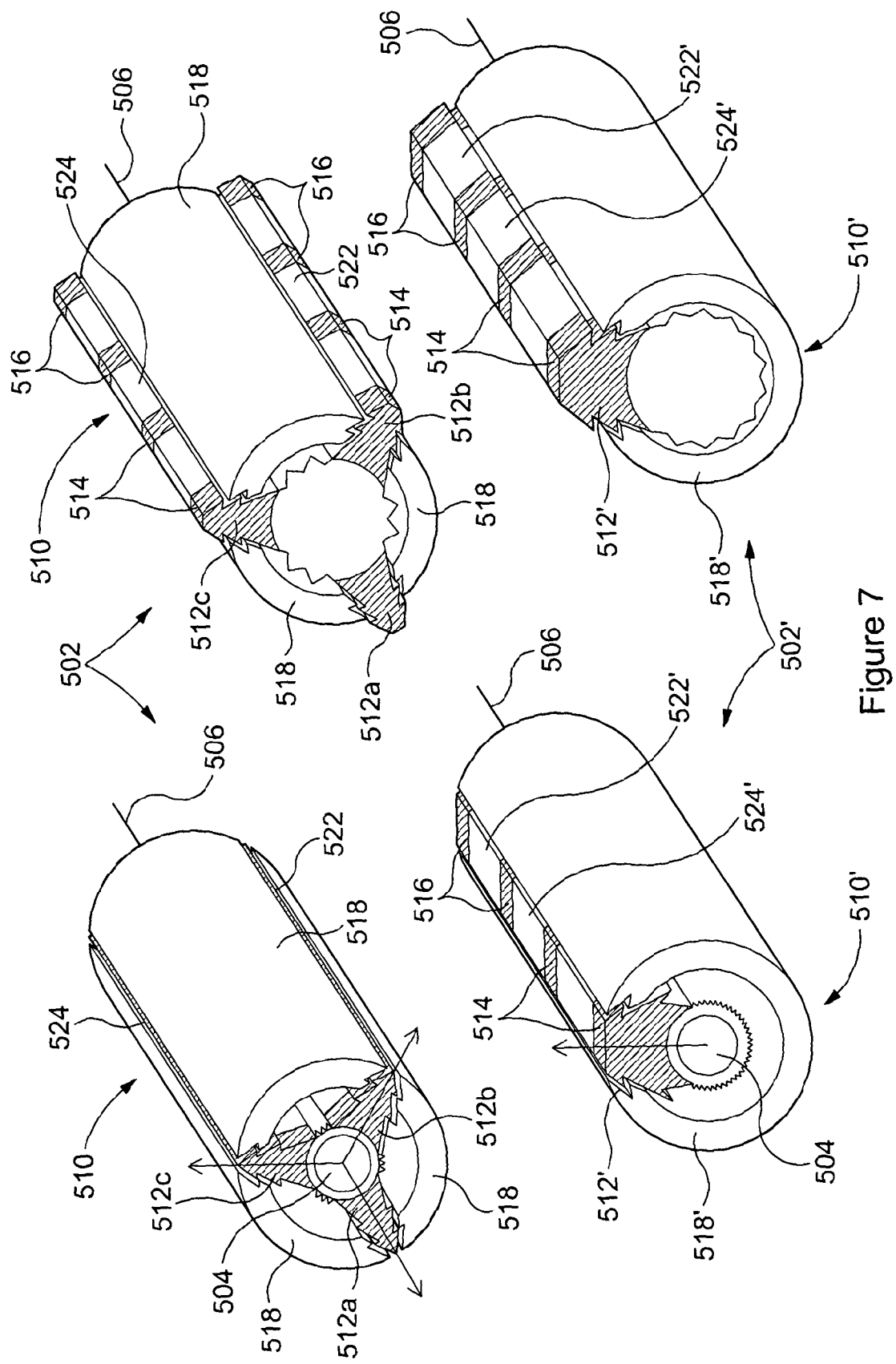
FIG. 7a is an elevational view from one end of a stimulation stent according to a fifth embodiment of the present invention in a condition ready to be deployed.
FIG. 7b is an elevational view from one end of the stimulation stent of FIG. 7a in a deployed condition.
FIG. 7c is an elevational view from one end of an alternative arrangement of the stimulation stent of FIG. 7a in a condition ready to be deployed.
FIG. 7d is an elevational view from one end of the stimulation stent of FIG. 7c in a deployed condition.

Turning to FIGS. 7a and 7b, there is shown a fifth embodiment of a stimulation stent, generally indicated as 502. The stent 502 is shown mounted on an angioplasty balloon 504 on a guide wire 506, in known manner, as it would be when being installed in the target vein.

The stent 502 comprises a generally cylindrical, expandable stent housing 510, shown extending around the balloon 504, on the angioplasty guide wire 506. The stent housing 510 comprises three circumferentially spaced electrode housings 512a, 512b, 512c, evenly spaced at a 120 degree orientation. Disposed between adjacent electrode housings is a flexible casing member 518, with two longitudinal ridges on each side. The electrode housings are attached loosely by a stented mesh to the flexible casing members 518 disposed therebetween. Each electrode housing 512 has a generally wedge-shaped cross-section, with two longitudinal ridges on each side to permit deployment of the electrode housings 512a, 512b and 512c against the flexible casing members 518 in a cam-like action by the action of the expanding balloon 504. The electrode housing 512a holds two pairs of electrodes 514, 516. When installed, the expansion of the balloon 504 using a cam mechanism urges the longitudinal ridges on the wedge-shaped electrode housings 512 radially outwards past the corresponding supporting longitudinal ridges on the flexible casing members 518. Consequently the electrodes 514, 516 in the housing 512a, 512b and 512c are urged into contact with the inner wall of the vein, in turn allowing electrical stimulation to be provided to the surrounding heart tissue. This embodiment allows two final deployment positions of the electrode housings 512, that is first position having a lesser diameter and a second position having a larger diameter, the diameter determined by the relative resting positions of the corresponding ridges on the electrode housings 512 and the flexible casing member 518. The selection of the position of the electrode housings 512 is dictated by the diameter of the target vein.

The electrode housings 512b and 512c contain further components for the operation of the stimulation stent, including an antenna (not shown for clarity) for receiving radio frequency signals from the controller 8, an electrical circuit 522, and requisite capacitors 524. The stent 502 is arranged to be powered by induction coupling, as is known in the art and, as a result, does not have a local power source, such as a battery. The stent of this embodiment is particularly suitable for positioning in larger diameter blood vessels.

As an alternative to providing power to each of the stimulation stents by induction, alternative means may be employed, such as acoustic coupling. Alternatively, or in addition, each stimulation stent may be provided with a local power storage device, in particular a battery. In particular, an alternative arrangement of the embodiment of FIGS. 7a and 7b provides for battery fittings within either of the electrode housings 512, in particular if radiofrequency communication is to be used. For example, the battery may occupy the entire inner space of the housing 512b and the circuitry may be accommodated in the housing component 512c. Alternative arrangements of the components may also be employed.

Referring to FIGS. 7c and 7c, there is shown an alternative arrangement of the stent of FIGS. 7a and 7b. The stent 502' of FIGS. 7c and 7d is similar in design to the stent 502 of FIGS. 7a and 7b, but has only one electrode housing 512'. The electrode housing is attached loosely by a stented mesh to the flexible casing member 518'. The deployment mechanism of the electrode housing 502' is similar to that of the stent 502 of FIGS. 7a and 7b, which is described above.

The electrode housing 512' contains further components for the operation of the stimulation stent, including an antenna (not shown for clarity) for receiving radio frequency signals from the controller 8, an electrical circuit 522', and requisite capacitors 524'

An alternative arrangement of the stent 502' of FIGS. 7c and 7d provides for battery fittings within the electrode housing 512', in particular if radiofrequency communication is to be used. Alternative arrangements of the components may also be employed.

Figure 8:
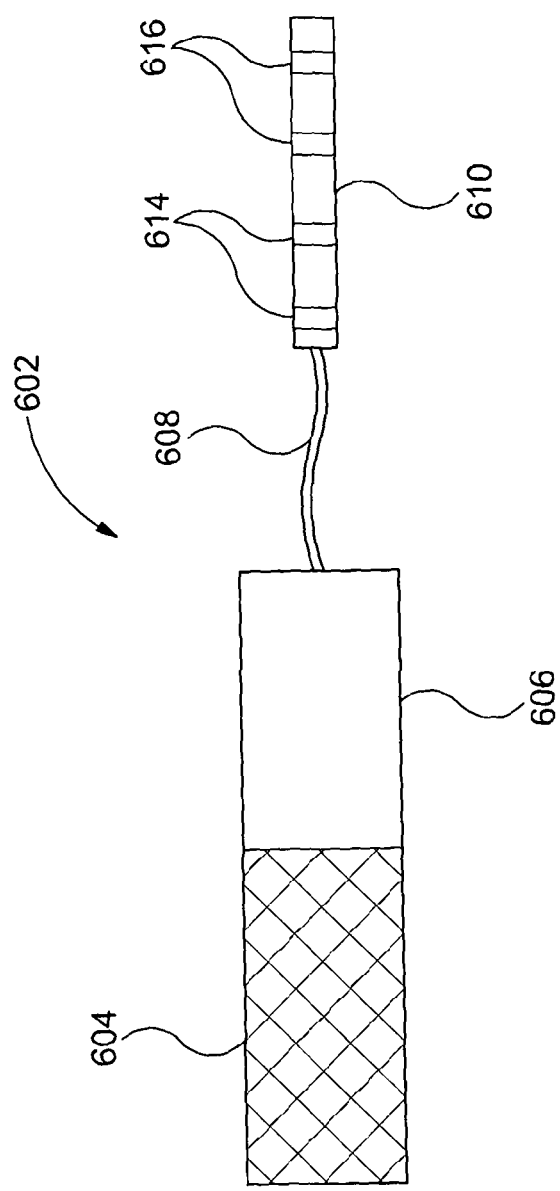
FIG. 8 is a side view of a stimulation stent according to a sixth embodiment of the present invention and intended for implanting in narrow or constricted veins.

Referring to FIG. 8, there is shown a further embodiment of a stimulation stent for use in the system of the present invention. The stimulation stent, generally indicated as 602, comprises a generally cylindrical, expandable body 604 of known configuration. When being installed, an angioplasty balloon and guide wire (not shown in FIG. 8 for clarity) are used in known manner and as described above. In particular, the stent body 604 is applied around the balloon and, when at the desired location in the vein, the balloon is inflated and the stent body expanded radially outwards, to thereby secure the body within the vein.

The stent 602 further comprises a generally cylindrical housing 606 mounted loosely to one end of the stent body 604 and extending longitudinally therefrom. The stent is installed with the housing 606 extending in a distal direction from the stent body 602. The housing 606 retains components, such as, for example circuitry, an antenna, capacitors and optionally a battery to act as a local power source.

A lead 608 extends from the end of the housing 606 in a distal direction within the vein, when installed, and terminates in an electrode assembly 610 comprising two pairs of electrodes 614, 616.

In use, the stent body 604 is installed in a portion of the target vein proximal of the target pacing site. Being proximal, this portion of the vein is generally larger in diameter and more accessible than the more remote pacing site. Once in situ, the lead 608 and electrode assembly 610 extend distally of the stent body 604 and the housing 606 into the narrower, distal portion of the vein, with the electrode assembly being located at the target site of the electrical stimulation.

Figure 9:
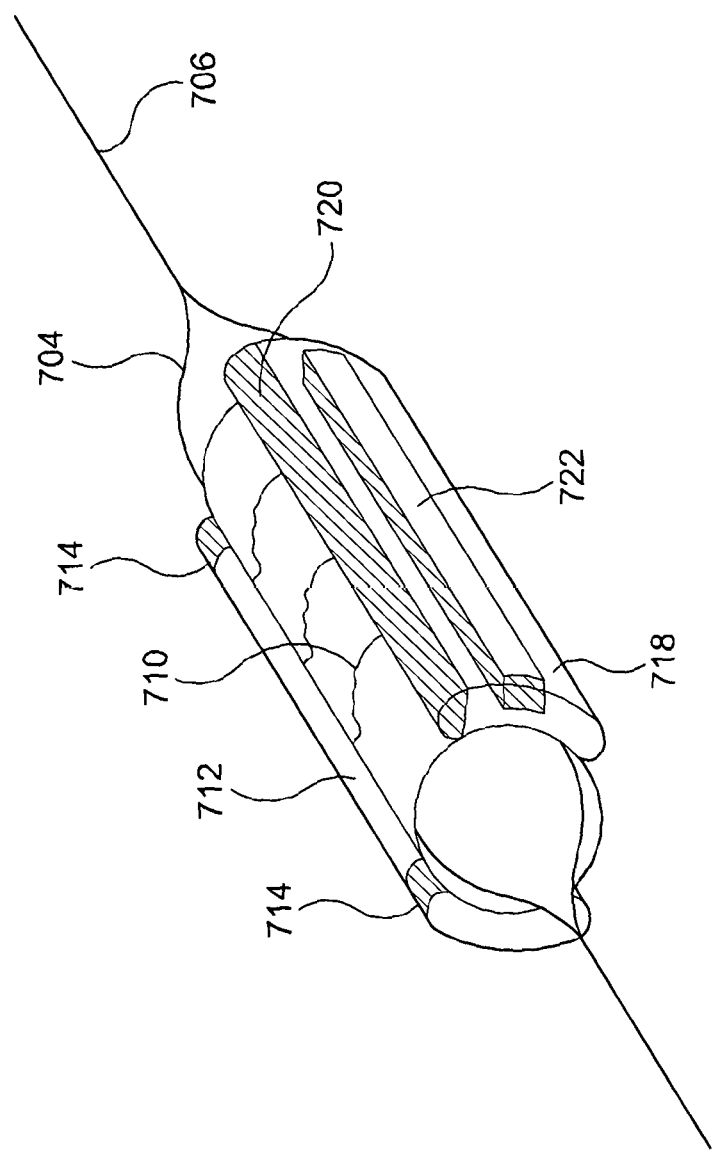
FIG. 9 is a perspective view of a first embodiment of a sensing stent for use in the system and method of the present invention.

Turning now to FIG. 9, there is shown a first embodiment of a sensing stent for implanting in the coronary sinus of the subject. The sensing stent, generally indicated as 702, is shown mounted on an angioplasty balloon 704 attached to a guide wire 706, in known manner, as it would be when being installed at the target location in the coronary sinus.

The sensing stent 702 comprises a generally cylindrical, expandable stent body 710 of known configuration, shown extending around the balloon 704, on an angioplasty wire 706. When being implanted, the stent body 710 is contracted and the balloon 704 deflated. To install the stent 702 at the target location, the balloon 704 is inflated in known manner, in turn expanding the stent body 710 radially outwards and securing the stent within the blood vessel. The balloon 704 is then deflated and removed, again in known manner.

An electrode housing 712 is mounted to one side of the stent body 710 and extends along and radially outwards from one side of the stent body. The housing 712 holds a pair of sensing electrodes 714. When installed, the expansion of the stent body 710 urges the sensing electrodes 714 radially outwards and into contact with the inner wall of the coronary sinus, in turn allowing electrical signals from the atrial and ventricular activity of the heart to be sensed.

A second housing 718 is disposed on the opposite side of the stent body to the electrode housing 712 and contains an antenna and transmitter assembly 720 for transmitting radio frequency signals to the controller 8, and a battery 722.

Figure 10:
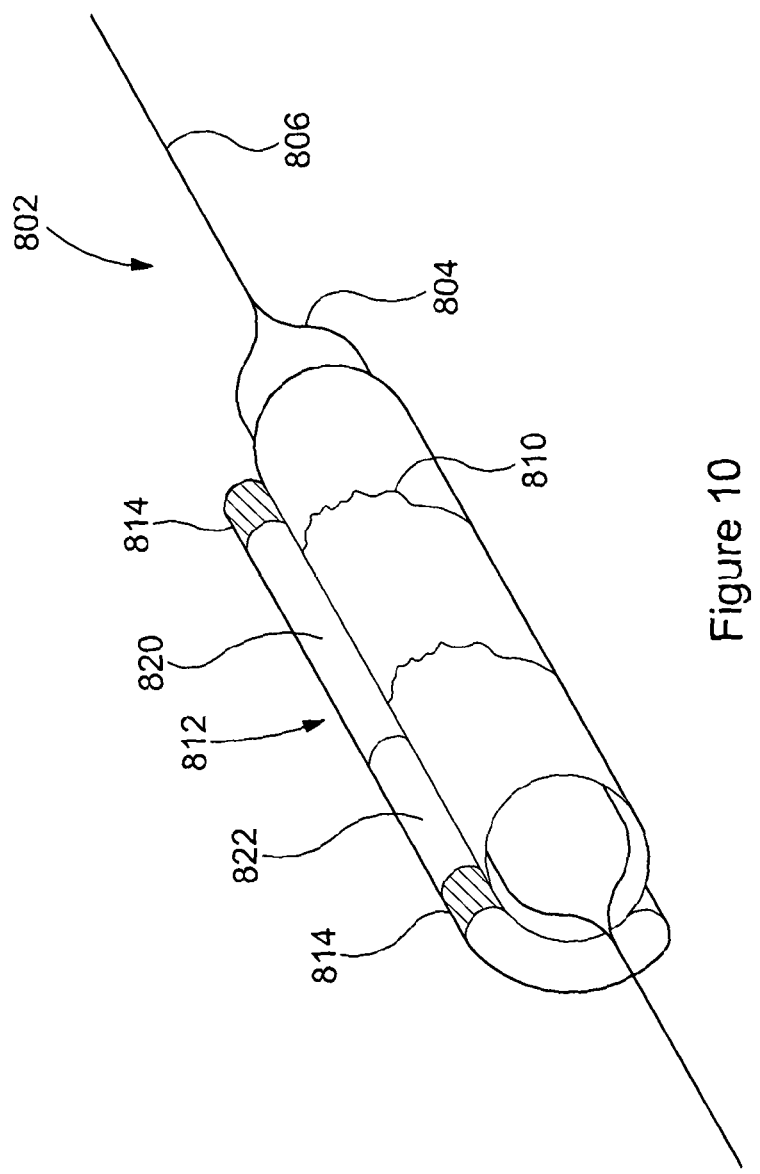
FIG. 10 is a perspective view of a second embodiment of a sensing stent for use in the system and method of the present invention.

Finally, referring to FIG. 10, there is shown a second embodiment of a sensing stent for implanting in the coronary sinus of the subject. The sensing stent, generally indicated as 802, is shown mounted on an angioplasty balloon 804 on an angioplasty guide wire 806, in known manner, as it would be when being installed at the target location in the coronary sinus.

The sensing stent 802 comprises a generally cylindrical, expandable stent body 810 of known configuration, shown extending around the balloon 804. The sensing stent 802 is installed in the coronary sinus of the subject in the manner described above in relation to FIG. 9.

A housing 812, having a generally arcuate cross-section, is mounted to one side of the stent body 810 and extends along and radially outwards from the one side of the stent body. The housing 812 holds a pair of sensing electrodes 814. When installed, the expansion of the stent body 810 urges the sensing electrodes 814 radially outwards and into contact with the inner wall of the coronary sinus, in turn allowing electrical signals from the atrial and ventricular activity of the heart to be sensed.

The housing 812 further contains an antenna and transmitter assembly 820 for transmitting radio frequency signals to the controller 8, and a battery 822.

The invention claimed is:

1. A method for providing stimulation to a heart of a subject, the heart comprising a coronary sinus having a proximal region with an ostium, a left atrium, a left ventricle, an oblique vein and a middle cardiac vein, the method comprising:
   sensing electrical activity of the heart at the ostium of the proximal region of the coronary sinus using a single sensing stent, the single sensing stent implanted in the coronary sinus, the sensing stent operable for sensing purposes only;
   transmitting first signal data from the ostium of the coronary sinus to a controller;
   generating second signal data for providing electrical stimulation to target tissue of the heart in response to the signal data received from the ostium of the coronary sinus transmitting the second signal data to a stimulation stent for stimulation of the target tissue, wherein the stimulation stent is located in a vein of the heart distal of the ostium of the coronary sinus; and
   providing electrical stimulation to the target tissue of the heart in response to the second signal data, wherein the electrical stimulation is provided to the tissue of the heart distal of the ostium of the coronary;
   wherein signal data are transmitted from the sensing stent to the controller and from the controller to the stimulation stent remotely without using leads.

2. The method according to claim 1, wherein pacing of the heart is provided at a single site.

3. The method according to claim 1, wherein the second signal data are transmitted to a plurality of stimulation stents.

4. The method according to claim 1, wherein electrical stimulation is provided to the left atrium of the heart.

5. The method according to claim 1, wherein electrical stimulation is provided to a mid to distal location of the coronary sinus.

6. The method according to claim 1, wherein electrical stimulation is provided to the left ventricle of the heart at a plurality of sites.

7. A method for the biventricular pacing of a heart of a subject, the heart comprising a coronary sinus having a proximal region with an ostium, a left ventricle and a right ventricle, the method comprising:
   sensing electrical activity of the heart at the ostium of the proximal region of the coronary sinus using a single sensing stent, the single sensing stent implanted in the coronary sinus, the sensing stent operable for sensing purposes only;
   transmitting first signal data from the ostium of the coronary sinus to a controller;
   generating second signal data for providing electrical stimulation to target tissue of the heart in response to the signal data received from the ostium of the coronary sinus;
   transmitting the second signal data to a plurality of stimulation stents disposed in a vein of the heart distal of the ostium of the coronary sinus for multisite stimulation of the left ventricle and stimulation stent disposed in a vein of the heart distal of the ostium of the coronary sinus for stimulation of the right ventricle; and
   providing electrical stimulation to both the left and right ventricles in response to the second signal data, wherein the electrical stimulation is provided to the tissue of the heart distal of the ostium of the coronary sinus;
   wherein signal data are transmitted from the sensing stent to the controller and from the controller to the stimulation stems remotely without using leads.

* * * * *